United States Patent
Wotton, III

(10) Patent No.: US 8,080,045 B2
(45) Date of Patent: Dec. 20, 2011

(54) BONE CLAMP

(76) Inventor: Harold M. Wotton, III, Woodstock, CT (US)

(*) Notice: Subject to any disclaimer, the term of this patent is extended or adjusted under 35 U.S.C. 154(b) by 925 days.

(21) Appl. No.: 12/082,034

(22) Filed: Apr. 8, 2008

(65) Prior Publication Data

US 2009/0254130 A1    Oct. 8, 2009

(51) Int. Cl.
  *A61B 17/56* (2006.01)
(52) U.S. Cl. ........................................ 606/324
(58) Field of Classification Search ............... 606/86, 606/205–208, 324
  See application file for complete search history.

(56) References Cited

U.S. PATENT DOCUMENTS

| | | | | |
|---|---|---|---|---|
| 5,578,032 A | * | 11/1996 | Lalonde | 606/54 |
| 5,851,207 A | * | 12/1998 | Cesarone | 606/86 B |
| 6,315,780 B1 | * | 11/2001 | Lalonde | 606/86 R |
| 6,589,241 B1 | * | 7/2003 | Townsend et al. | 606/54 |
| 6,679,888 B2 | | 1/2004 | Green et al. | |
| 6,730,086 B2 | * | 5/2004 | Hehli et al. | 606/54 |
| RE38,684 E | * | 1/2005 | Cesarone | 606/915 |
| 2004/0013999 A1 | * | 1/2004 | Sussman | 433/75 |
| 2007/0244516 A1 | * | 10/2007 | Chiu et al. | 606/207 |

OTHER PUBLICATIONS

Lalonde, Donald H., A Bone Clamp. Can J. Plast Surg. vol. 6, No. 2, 1998, pp. 105-106 (4 pages).
Lalonde, Donald H., Dynamic Compression Bone Clamp for Transverse Fractures. Can J. Plast Surg. vol. 8, No. 2, Mar./Apr. 2000 (3 pages).
Accurate Surgical & Scientific Instrucments Corporation. ASSI Lalonde Bone Clamps. http://www.accuratesurgical.com/accuratesurgical/Docs/BoneClamp1a.html, (printed Aug. 29, 2007) (1 page).

* cited by examiner

*Primary Examiner* — Suzette J Gherbi
(74) *Attorney, Agent, or Firm* — Iandiorio Teska & Coleman

(57) ABSTRACT

A bone clamp, in one example, includes a first scissor arm and a second scissor arm pivotally connected to the first scissor arm. A guide is pivotally attached to the first scissor arm and a first clamping member with a drill or wire receiving channel therethrough is pivotally connected to the second scissor arm and slideable through the guide. A second clamping member is fixed to the guide. In this way, when a bone is clamped between the first and second clamping members, a drill and/or wire can proceed through the first clamping member and into the bone between the first and second clamping members.

16 Claims, 5 Drawing Sheets

US 8,080,045 B2

BONE CLAMP

FIELD OF THE INVENTION

This invention relates to a bone clamp.

BACKGROUND OF THE INVENTION

A variety of bone clamps are known. U.S. Pat. No. 5,578,032, for example, discloses a scissors like instrument with a pin on one scissor arm slideable through a tube on the other scissor arm. The "Lalonde" bone clamp (Accurate Surgical & Scientific Instruments, Corp., Westbury, N.Y.) is similar but also includes a wire guide on the tube.

In some medical procedures, a bone held by a clamp is drilled. One common example involves the use of a pin placed in the drilled bone hole to secure a ligament to the bone. Using conventional bone clamps, the drilling axis is offset from the clamping axis.

It would be advantageous if a bone clamp allowed the drilling axis to be the same as the clamping axis.

BRIEF SUMMARY OF THE INVENTION

It is therefore an object of this invention to provide a new bone clamp.

It is a further object of this invention to provide such a bone clamp which, when used, ensures the drilling axis is the same as clamping axis.

The subject invention results from the realization, in part, that one preferred embodiment of a bone clamp is engineered so that a clamping member slideable through a guide includes a drill channel so the drilling axis is the same as the clamping axis for more precise operations.

The subject invention features a bone clamp typically with a first scissor arm and a second scissor arm pivotally connected to the first scissor arm. A guide is pivotally attached to the first scissor arm and a first clamping member with a drill or wire receiving channel therethrough is pivotally connected to the second scissor arm and slideable through the guide. A second clamping member is fixed to the guide so that when a bone is clamped between the first and second clamping members, a drill or wire can proceed through the first clamping member and into the bone between the first and second clamping members.

In one preferred embodiment, the first scissor arm includes a first proximal finger loop and the second scissor arm includes a second proximal finger loop. Also, the first scissor arm includes a ratchet tang and the second scissor arm includes a ratchet cog. In one example, the guide includes a first tab, the distal end of the first scissor arm includes a slot which receives the first tab, and there is a pin pivotally connecting the distal end of the first scissor arm to the first tab. Also, the first clamping member may include a second tab, the distal end of the second scissor arm includes a slot which receives the second tab, and there is a pin pivotally connecting the distal end of the second scissor arm to the second tab.

Preferably, the distal end of the first clamping member is tapered and includes teeth, and the proximal end of the second clamping member is also tapered and also includes teeth. A curved arm, which may be adjustable, preferably fixes the second clamping member to the guide and is shaped to align the second clamping member with the first clamping member. Also, it is preferred that the second clamping member includes a drill receiving channel therethrough so that the drill can proceed through the bone.

One bone clamp in accordance with the subject invention includes a first arm, a second arm, a guide attached to the distal end of the first arm, and a first clamping member with a drill or wire receiving channel therethrough connected to the second arm and slideable through the guide. A second clamping member includes a drill receiving channel therethrough. A curved arm fixes the second clamping member to the guide and is shaped to align the second clamping member with the first clamping member.

A clamping device comprising a pair of clamping members actionable to clamp an item therebetween and defining a clamping axis and configured to define a drilling axis the same as or approximately the same as the clamping axis.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
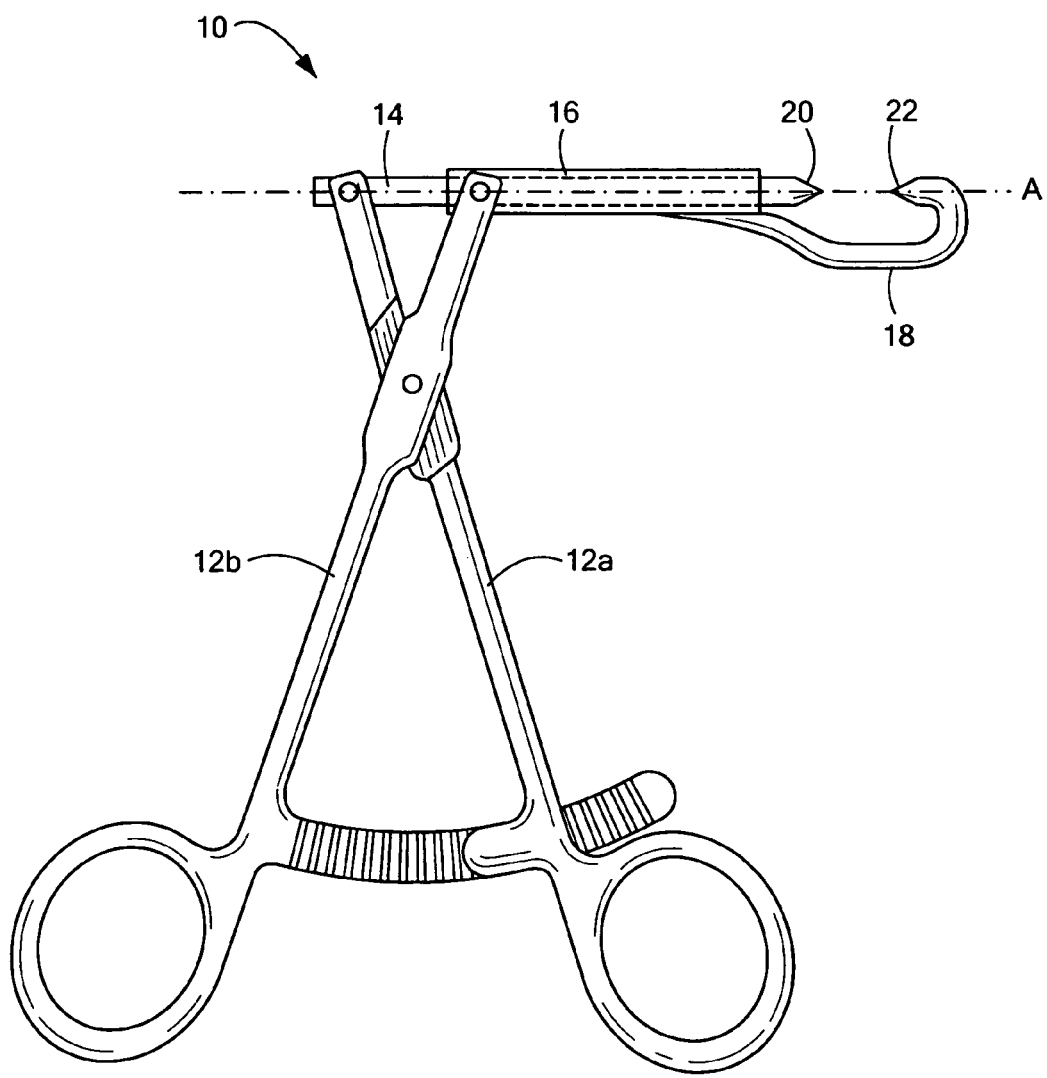
FIG. 1 is a schematic front view of a prior art bone clamp.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows prior art bone clamp 10 of U.S. Pat. No. 5,578,032 incorporated herein by this reference. Scissor arm 12a is connected to pin 14 which slides through tube 16 connected to scissor arm 12b. Hook 18 is attached to tube 16 defining bone clamping axis A for a bone between tip 20 of pin 14 and tip 22 of hook 18.

Figure 3:
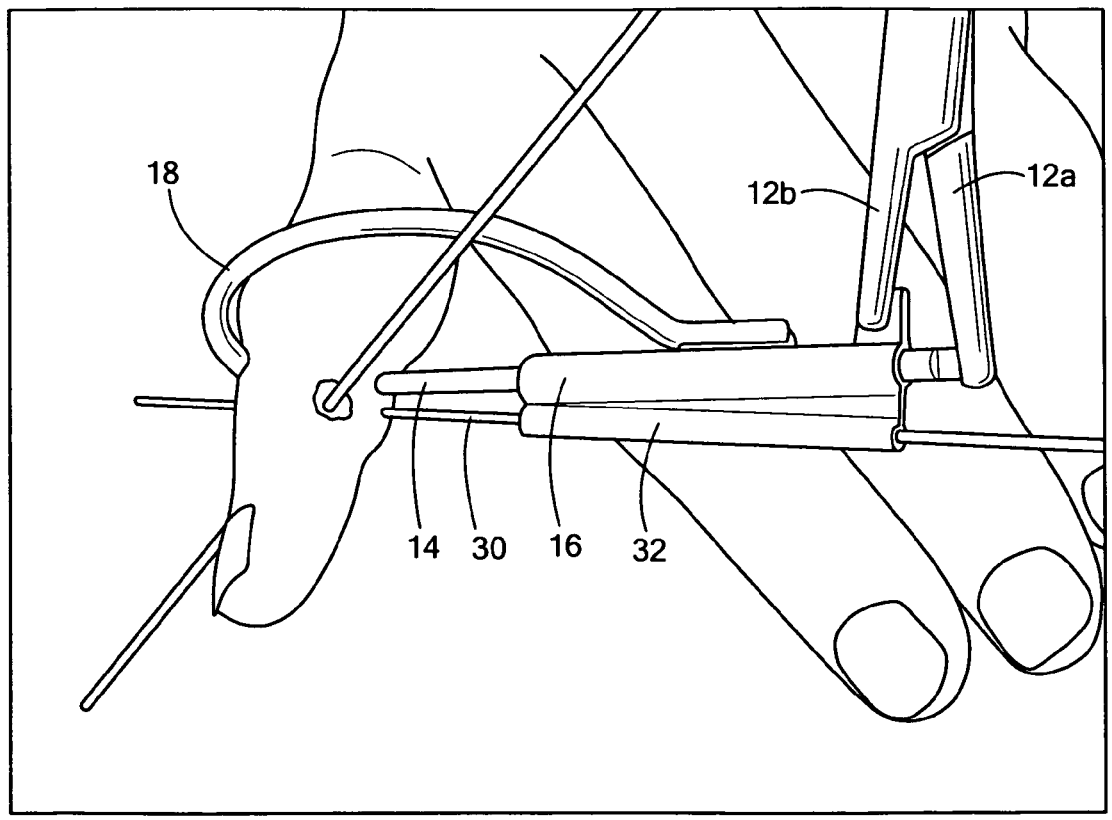
FIG. 3 is a schematic three-dimensional view showing the bone clamp of FIG. 2 used to insert a wire through a bone.

Another similar prior art device 10a, FIG. 3 includes wire guide 30 on tube 16 with tunnel 32 for a "K Wire." This bone clamp is commercially called the "Lalonde" bone clamp. Note that wire axis W defined by tunnel 32 is significantly offset from clamp axis A. FIG. 3 shows this bone clamp in use with K-Wire 30 inserted through tunnel 32 and into a finger bone clamped between pin 14 and hook 18.

Figure 4:
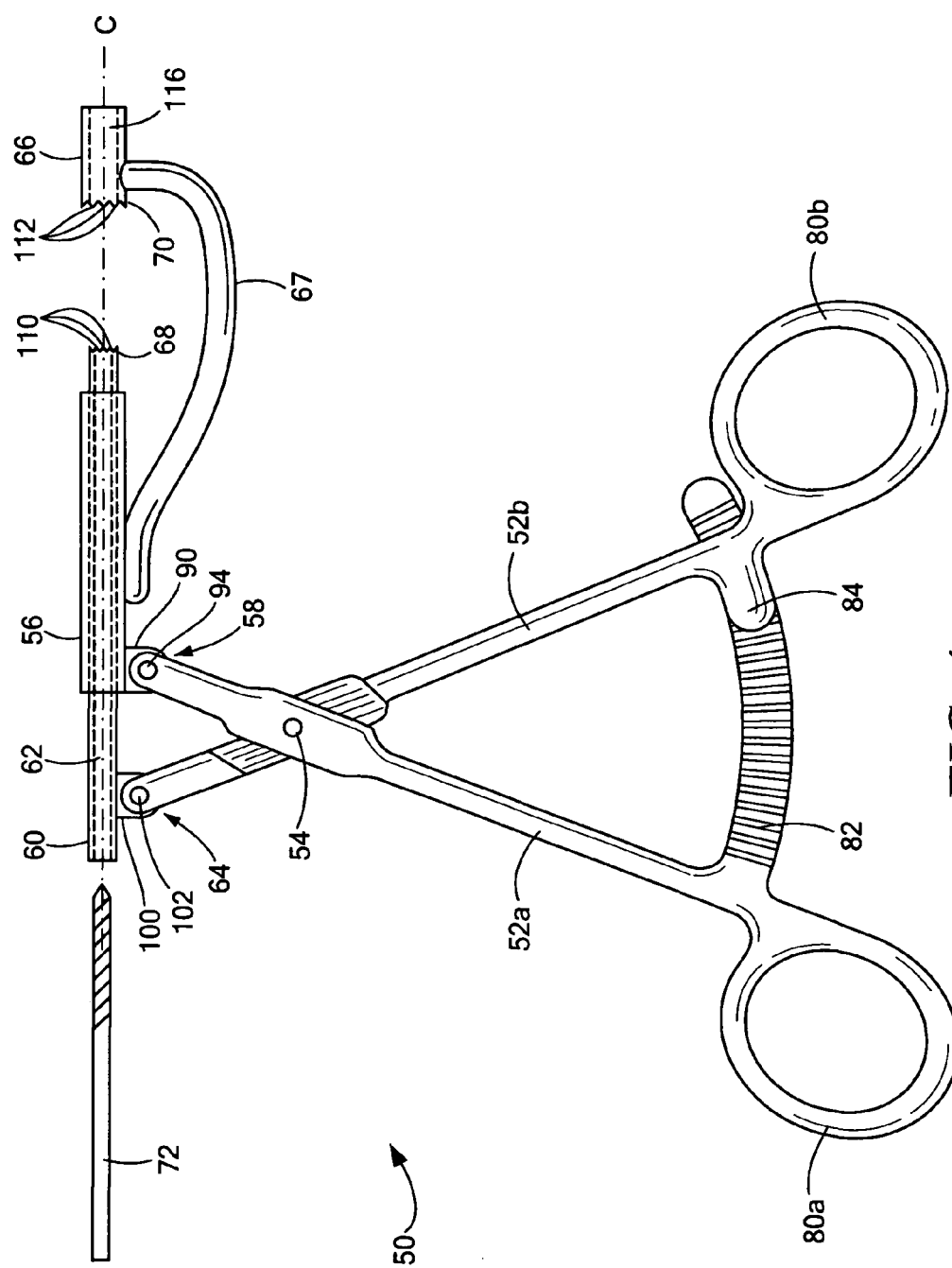
FIG. 4 is a schematic front view of an example of a bone clamp in accordance with the subject invention.

Bone clamp 50, FIG. 4, in accordance with an embodiment of the subject invention, includes first scissor arm 52a pivotally connected to second scissor arm 52b via pin 54. Guide 56 is pivotally attached to the distal end 58 of first scissor arm 52a. Clamping member 60 has a drill or wire receiving channel 62 therethrough and is pivotally connected to the distal end 64 of second scissor arm 52b. Clamping member 66 is fixed to guide 56 via curved arm 67 shaped to align clamping members 60 and 66 along clamping axis C.

In this way, when a bone is clamped between the distal end 68 of clamping member 60 and the proximal end 70 of clamping member 66, drill 72 (and/or a wire) can proceed through first clamping member 60 and into the bone along the clamping axis C.

In one particular example, sliding clamping member 60 is round and 2.7 mm in diameter. Channel 62 is 1.5 mm in diameter and can thus accommodate a 1.1 mm drill 72.

Typically, first scissor arm 52a preferably includes proximal finger loop 80a and second scissor arm 52b includes proximal finger loop 80b. Also, first scissor arm 52a preferably includes ratchet tang 82 with teeth which cooperate with the teeth on ratchet cog on second scissor arm 52b. Guide 56 includes tab 90 received in slot 92 in scissor arm 52a. Pin 94 pivotally connects the distal end 58 of scissor arm 52a to tab 90. Similarly, clamp 60 includes tab 100 received in a slot in the distal end of scissor arm 52b and pin 102 pivotally connects the distal end 64 of scissor arm 52b to tab 100.

Although the design of the clamping members may vary, in one preferred embodiment, the distal end 68 of first clamping member 60 includes teeth 110 and the proximal end 70 of clamping member 66 includes teeth 112.

Figure 2:
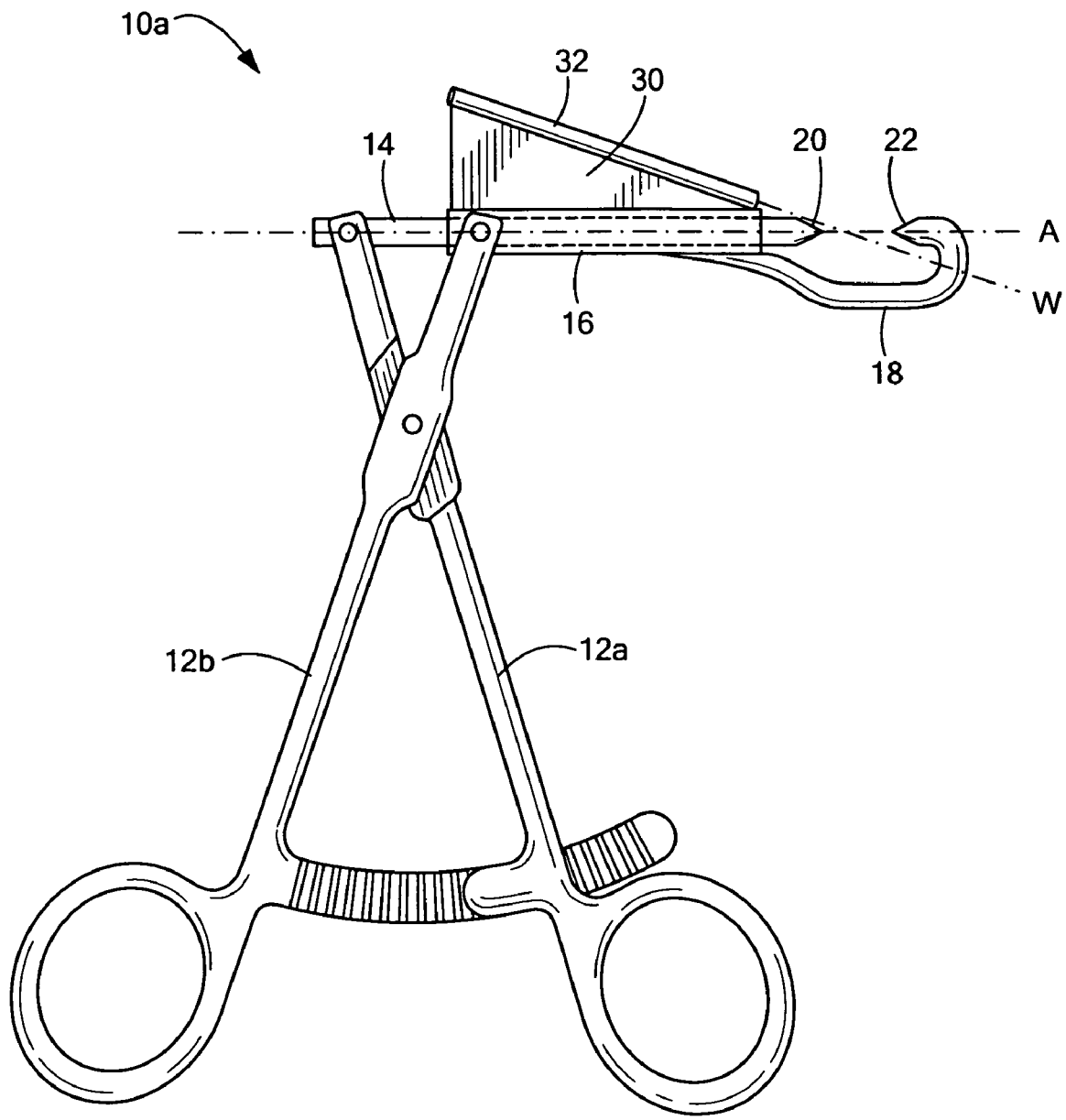
FIG. 2 is a schematic front view of another example of a prior art bone clamp.

Clamping member 66 preferably also includes a drill receiving channel 116 therethrough so drill 72 (and/or a wire) can pass through clamping member 66. Note that in FIGS. 1-2, it is not possible, in accordance with the prior art, for a drill or wire to pass through either pin 20 or hook 18. The subject invention, in contrast, features a bone clamp with the drilling axis the same as the clamping axis.

Figure 5:
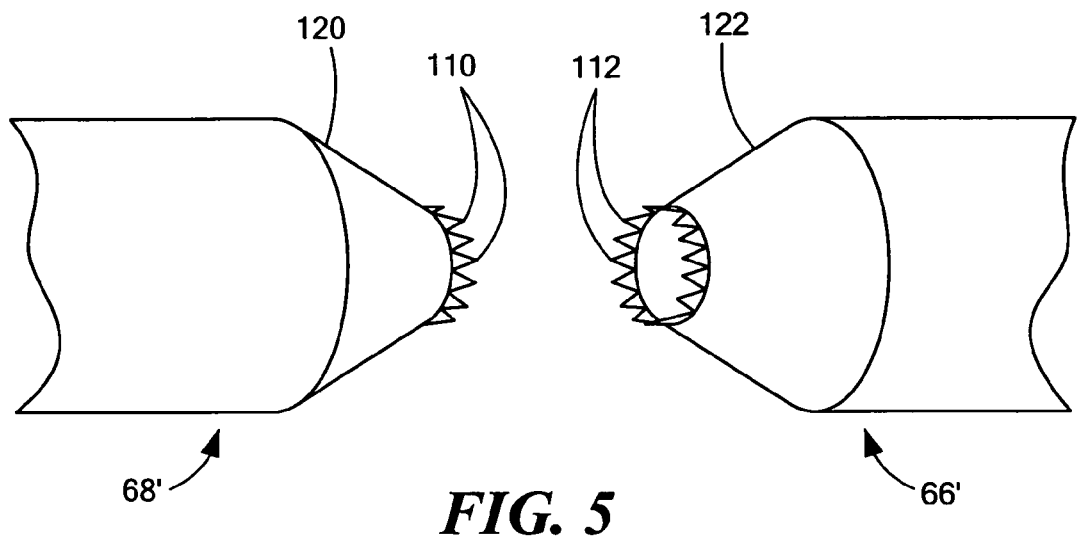
FIG. 5 is a schematic front view showing tapered clamping members in accordance with the subject invention.

FIG. 5 shows clamping member 68' with a distal end taper 120 and clamping member 66' with a proximal end taper 122.

Figure 6:
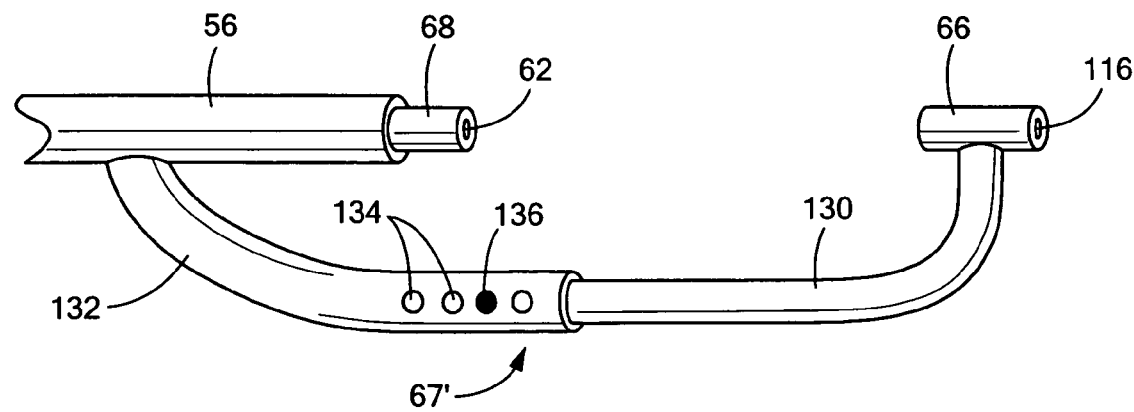
FIG. 6 is a schematic front view showing an adjustable arm in accordance with the subject invention.

FIG. 6 shows adjustable arm 67' securing clamping member 66 to guide 56. Arm 67' includes section 130 telescopingly received in section 132 which includes spaced orifices 134 receiving spring loaded ball 136 on section 130. In this way, bones of different sizes can be accommodated. In one example, the arm can be adjusted so the maximum gap between clamping members 68 and 66 ranges from 40 mm to 60 mm.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A bone clamp comprising:
a first scissor arm;
a second scissor arm pivotally connected to the first scissor arm;
a guide pivotally attached to the first scissor arm;
a first clamping member with a drill receiving channel therethrough or with a wire receiving channel therethrough, the first clamping member pivotally connected to the second scissor arm and slideable within the guide; and
a second clamping member fixed to the guide so that when a bone is clamped between the first and second clamping members, a drill and/or wire can proceed through the channel in the first clamping member and into the bone between the first and second clamping members.

2. The bone clamp of claim 1 of which the first scissor arm includes a first proximal finger loop and the second scissor arm includes a second proximal finger loop.

3. The bone clamp of claim 1 in which the first scissor arm includes a ratchet tang and the second scissor arm includes a ratchet cog.

4. The bone clamp of claim 1 in which the guide includes a first tab, the distal end of the first scissor arm includes a slot which receives the first tab, and there is a pin pivotally connecting the distal end of the first scissor arm to the first tab.

5. The bone clamp of claim 1 in which the first clamping member includes a second tab, the distal end of the second scissor arm includes a slot which receives the second tab, and there is a pin pivotally connecting the distal end of the second scissor arm to the second tab.

6. The bone clamp of claim 1 in which a distal end of the first clamping member includes teeth.

7. The bone clamp of claim 1 in which a proximal end of the second clamping member includes teeth.

8. The bone clamp of claim 1 further including a curved arm fixing the second clamping member to the guide and shaped to align the second clamping member with the first clamping member.

9. The bone clamp of claim 8 in which the curved arm is adjustable.

10. The bone clamp of claim 1 in which the second clamping member includes a drill receiving channel or wire receiving channel therethrough so that the drill can proceed through the bone.

11. The bone clamp of claim 1 in which a distal end of the first clamping member and a proximal end of the second clamping member includes a taper.

12. A bone clamp comprising:
a first scissor arm;
a second scissor arm pivotally connected to the first scissor arm;
a guide pivotally attached to the distal end of the first scissor arm;
a first clamping member with a drill receiving channel therethrough or with a wire receiving channel therethrough, the first clamping member pivotally connected to a distal end of the second scissor arm and slideable within the guide;
a second clamping member; and
a curved arm fixing the second clamping member to the guide and shaped to align the second clamping member with the first clamping member.

13. The bone clamp of claim 12 in which the curved arm is adjustable.

14. A bone clamp comprising:
a first arm;

a second arm connected to the first arm;
a guide attached to the first arm;
a first clamping member with a drill receiving channel or wire receiving channel therethrough, the first clamping member connected to the second arm and slideable through the guide; and
a second clamping member fixed to the guide and with a drill receiving channel or wire receiving channel therethrough so that when a bone is clamped between the first and second clamping members, a drill and/or wire can proceed through the clamping members and through the bone between the first and second clamping members.

15. A bone clamp comprising:
a first arm;
a second arm;
a guide attached to the distal end of the first arm;
a first clamping member with a drill receiving channel or wire receiving channel therethrough connected to the second arm and slideable through the guide;
a second clamping member including a drill receiving channel or wire receiving channel therethrough; and
a curved arm fixing the second clamping member to the guide and shaped to align the second clamping member with the first clamping member.

16. A clamping device comprising a pair of clamping members actuatable to clamp an item therebetween and defining a clamping axis and configured to define a drilling axis the same as or approximately the same as the clamping axis.

* * * * *